(12) United States Patent
Eyal et al.

(10) Patent No.: US 11,306,339 B2
(45) Date of Patent: Apr. 19, 2022

(54) METHOD FOR THE PRODUCTION OF A RHAMNOLIPID

(71) Applicants: Superbrewed Food, Inc., New Castle, DE (US); Aharon M. Eyal, Jerusalem (IL); Bryan P. Tracy, Wilmington, DE (US); Christopher Joseph McWilliams, Somerville, MA (US)

(72) Inventors: Aharon M. Eyal, Jerusalem (IL); Bryan P. Tracy, Wilmington, DE (US); Christopher Joseph McWilliams, Somerville, MA (US)

(73) Assignee: SUPERBREWED FOOD, INC., New Castle, DE (US)

(*) Notice: Subject to any disclaimer, the term of this patent is extended or adjusted under 35 U.S.C. 154(b) by 380 days.

(21) Appl. No.: 16/310,152

(22) PCT Filed: Jun. 16, 2017

(86) PCT No.: PCT/US2017/037845
§ 371 (c)(1),
(2) Date: Mar. 26, 2019

(87) PCT Pub. No.: WO2017/218875
PCT Pub. Date: Dec. 21, 2017

(65) Prior Publication Data
US 2019/0241922 A1    Aug. 8, 2019

Related U.S. Application Data

(60) Provisional application No. 62/351,034, filed on Jun. 16, 2016.

(51) Int. Cl.
| | |
|---|---|
| *C12P 19/44* | (2006.01) |
| *C07H 1/08* | (2006.01) |
| *C07H 15/04* | (2006.01) |
| *A61K 8/60* | (2006.01) |
| *C12P 7/6409* | (2022.01) |
| *A61K 8/04* | (2006.01) |
| *A61K 9/00* | (2006.01) |
| *A61K 9/12* | (2006.01) |
| *A61Q 19/00* | (2006.01) |

(52) U.S. Cl.
CPC .............. *C12P 19/44* (2013.01); *A61K 8/046* (2013.01); *A61K 8/602* (2013.01); *A61K 9/0014* (2013.01); *A61K 9/122* (2013.01); *A61Q 19/00* (2013.01); *C07H 1/08* (2013.01); *C07H 15/04* (2013.01); *C12P 7/6409* (2013.01)

(58) Field of Classification Search
None
See application file for complete search history.

(56) References Cited

U.S. PATENT DOCUMENTS

| | | | |
|---|---|---|---|
| 2004/0082042 A1 | 4/2004 | Staley | |
| 2011/0306569 A1* | 12/2011 | Yin | C12P 7/6463 514/25 |
| 2014/0148588 A1 | 5/2014 | Schilling et al. | |
| 2014/0235561 A1 | 8/2014 | Blank et al. | |

FOREIGN PATENT DOCUMENTS

| | | |
|---|---|---|
| WO | 2015/134246 | 9/2015 |
| WO | 2016/160812 | 10/2016 |

OTHER PUBLICATIONS

International Search Report in International Patent Application No. PCT/US2017/37845, dated Sep. 28, 2017.
U.S. Appl. No. 62/351,034, filed Jun. 16, 2016.
International Preliminary Report on Patentability issued with respect to Patent Application No. PCT/US2017/37845, dated Dec. 18, 2018.

* cited by examiner

*Primary Examiner* — Michelle F. Paguio Frising
(74) *Attorney, Agent, or Firm* — Eva Taksel

(57) ABSTRACT

A method for the production of a rhamnolipid. The method includes culturing in a fermentation medium an organism capable of producing a rhamnolipid to form a fermentation broth comprising at least one rhamnolipid and having a pH>5; extracting at least one lipophilic impurity from said fermentation broth; acidulating said fermentation broth to form an aqueous medium of pH<5 comprising the at least one rhamnolipid; extracting the at least one rhamnolipid from said acidulated fermentation broth; and separating the at least one rhamnolipid to obtain a purified rhamnolipid.

17 Claims, No Drawings

METHOD FOR THE PRODUCTION OF A RHAMNOLIPID

CROSS-REFERENCE TO RELATED APPLICATION

The pending application claims the benefit of priority to U.S. Provisional Application No. 62/351,034 filed Jun. 16, 2016, the disclosure of which is expressly incorporated by reference in its entirety.

FIELD OF THE INVENTION

The invention relates to the production of lipids comprising at least one rhamnose sugar moiety.

BACKGROUND

Rhamnolipids are a class of glycolipids, typically carrying one or two rhamnose head group moieties (which may be designated "R" and "RR," respectively) and one or two fatty acids tails (which may be designated "L" or "LL," respectively) such that a rhamnolipid comprising two rhamnose head groups and two fatty acids may be designated "RRLL". Many of the rhamnolipids fall into one of four categories according to the number of R and L groups: (1) RL, (2) RRL, (3) RLL and (4) RRLL. Rhamnolipids are surfactants.

Rhamnolipids are products of fermentation and as such belong to only a few bio-surfactants in commerce.

Fermentation generates a fermentation broth of relatively low rhamnolipids concentration, containing many impurities, including residual carbon source and nitrogen source, fatty acids, colored compounds and in some cases also antifoam agents. Some of those impurities are particularly difficult to remove, for example triglycerides, fatty acids and antifoam agents. Low-cost methods for the production of purified and concentrated rhamnolipids are highly desired.

SUMMARY OF THE INVENTION

A method for production of a rhamnolipid is described including (i) providing an aqueous fermentation medium comprising a carbon source and a nitrogen source; (ii) culturing in said fermentation medium an organism capable of producing a rhamnolipid, wherein said carbon source is metabolized to form a fermentation broth having a pH greater than 5 and comprising at least one rhamnolipid, at least one lipophilic impurity, and at least one hydrophilic impurity; (iii) extracting at least one lipophilic impurity from said fermentation broth with a first extractant to form (a) a lipophilic-impurity-depleted fermentation broth comprising the at least one rhamnolipid and (b) a first extract comprising said first extractant and said at least one lipophilic impurity; (iv) acidulating said lipophilic-impurity-depleted fermentation broth to form an acidulated lipophilic-impurity-depleted aqueous medium of pH less than 5 comprising the at least one rhamnolipid; (v) extracting the at least one rhamnolipid from said acidulated lipophilic-impurity-depleted aqueous medium with a second extractant to obtain a second extract comprising said second extractant and the at least one rhamnolipid; and (vi) separating the at least one rhamnolipid from said second extract to obtain a purified rhamnolipid.

Additional embodiments include: the method described above comprising separating the first extractant and the at least one lipophilic impurity from the first extract; the method described above where said carbon source comprises a triglyceride; the method described above where said organism capable of producing a rhamnolipid is a *Pseudomonas* strain; the method described above where the *Pseudomonas* strain is selected from the group consisting of *Pseudomonas aeruginosa, Pseudomonas chlororaphis*, and *Pseudomonas putida*; the method described above where said organism capable of producing a rhamnolipid is a *Burkholderia* strain; the method described above where the *Burkholderia* strain is selected from the group consisting of *Burkholderia mallei, Burkholderia pseudomallei*, and *Burkholderia thailandensis*; the method described above where said organism capable of producing a rhamnolipid is selected from the group consisting of *Acinetobacter calcoaceticus, Enterobacter asburiae, Enterobacter hormaechei, Pantoea stewartii, Thermus aquaticus, Meiothermus ruber*, and *Tetragenococcus koreensis*; the method described above where said at least one rhamnolipid comprises one rhamnose moiety in combination with two fatty acid chains and/or two rhamnose moieties in combination with two fatty acid chains; the method described above where rhamnolipid concentration in said fermentation broth having a pH greater than 5 is in the range between 1 g/l and 70 g/l; the method described above where said first extractant, said second extractant, or both comprise at least one of (a) a hydrocarbon having a boiling point under 20° C. at atmospheric pressure, and (b) an oxygenated organic compound having a boiling point under 20° C. at atmospheric pressure, wherein said oxygenated organic compound has a Hansen solubility parameter polarity component in the range between 2 $MPa^{0.5}$ and 8 $MPa^{0.5}$ and a Hansen solubility parameter H-bond component in the range between 2 $MPa^{0.5}$ and 8 $MPa^{0.5}$; the method described above where both said first extractant and said second extractant comprise at least one of said hydrocarbon and said oxygenated organic compound; the method described above where said hydrocarbon is an olefin; the method described above where said oxygenated organic compound is selected from the group consisting of dimethyl ether, methyl-ethyl ether, diethyl ether and combinations thereof; the method described above where said first extractant, said second extractant or both comprise said oxygenated organic compound and an olefin with a boiling point under 20° C. while at atmospheric pressure; the method described above where said first extractant comprises an olefin and said second extractant comprises said oxygenated organic compound; the method described above where said separating said first extractant, said separating said second extractant, or both comprises evaporation; the method described above further comprising liquefying at least a fraction of the separated first and/or separated second extractant, wherein said liquefying comprises subjecting said at least a fraction of the separated first and/or separated second extractant to a refrigerant circuit; the method described above where a refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

Purified rhamnolipid produced according to the method described above, and a detergent, cosmetic or topical pharmaceutical product comprising the purified rhamnolipid produced according to the method described above, are also described.

A method for production of a rhamnolipid is also described including (i) providing an aqueous fermentation medium comprising a carbon source and a nitrogen source;

(ii) culturing in said fermentation medium an organism capable of producing a rhamnolipid, wherein said carbon source is metabolized to form a fermentation broth having a pH greater than 5 and comprising at least one rhamnolipid, at least one lipophilic impurity and at least one hydrophilic impurity; (iii) acidulating said fermentation broth to form an acidulated aqueous medium of pH less than 5; (iv) extracting the at least one rhamnolipid and the at least one lipophilic impurity from said acidulated aqueous medium with a first extractant, thereby obtaining a hydrophilic-impurity-depleted first extract comprising the at least one rhamnolipid, the at least one lipophilic impurity and the first extractant; (v) separating said first extractant from said at least one rhamnolipid and said at least one lipophilic impurity in said first extract to obtain a separated medium comprising said at least one rhamnolipid and said at least one lipophilic impurity; (vi) adjusting the pH of the separated medium to a pH greater than 5; and (vii) extracting the at least one lipophilic impurity from said pH-adjusted separated medium with a second extractant to obtain purified rhamnolipid.

Additional embodiments include: the method described above where said extracting the at least one lipophilic impurity comprises forming a second extract comprising the second extractant and the at least one lipophilic impurity; the method described above further comprising separating the second extractant and the at least one lipophilic impurity from the second extract; the method described above where said carbon source comprises a triglyceride; the method described above where said organism capable of producing a rhamnolipid is a *Pseudomonas* strain; the method described above where the *Pseudomonas* strain is selected from the group consisting of *Pseudomonas aeruginosa*, *Pseudomonas chlororaphis*, and *Pseudomonas putida*; the method described above where said organism capable of producing a rhamnolipid is a *Burkholderia* strain; the method described above where the *Burkholderia* strain is selected from the group consisting of *Burkholderia mallei*, *Burkholderia pseudomallei*, and *Burkholderia thailandensis*; the method described above where said organism capable of producing a rhamnolipid is selected from the group consisting of *Acinetobacter calcoaceticus*, *Enterobacter asburiae*, *Enterobacter hormaechei*, *Pantoea stewartii*, *Thermus aquaticus*, *Meiothermus ruber*, and *Tetragenococcus koreensis*; the method described above where said at least one rhamnolipid comprises one rhamnose moieties in combination with two fatty acid chains, and/or two rhamnose moieties in combination with two fatty acid chains; the method described above where rhamnolipid concentration in said fermentation broth is in the range between 1 g/l and 70 g/l; the method described above where said first extractant, said second extractant, or both comprise at least one of (a) a hydrocarbon having a boiling point under 20° C. while at atmospheric pressure and (b) an oxygenated organic compound having a boiling point under 20° C. at atmospheric pressure, wherein said oxygenated organic compound has a Hansen solubility parameter polarity component in the range between 2 $MPa^{0.5}$ and 8 $MPa^{0.5}$ and a Hansen solubility parameter H-bond component in the range between 2 $MPa^{0.5}$ and 8 $MPa^{0.5}$; the method described above where said hydrocarbon is an olefin; the method described above where said oxygenated organic compound is selected from the group consisting of dimethyl ether, methyl-ethyl ether, diethyl ether and combinations thereof; the method described above where said separating said first extractant comprises evaporation; the method described above further comprising liquefying at least a fraction of the separated first extractant, wherein said liquefying comprises subjecting said at least a fraction of the separated first extractant to a refrigerant circuit; the method described above where a refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

Purified rhamnolipid produced according to the method described above, and a detergent, cosmetic or topical pharmaceutical product comprising the purified rhamnolipid produced according to the method described above, are also described.

A method for the production of a rhamnolipid is also described including (i) providing a fermentation medium comprising a carbon source and a nitrogen source; (ii) culturing in said fermentation medium an organism capable of producing a rhamnolipid, wherein said carbon source is metabolized to form a fermentation broth having a pH greater than 5 and comprising at least one rhamnolipid, at least one lipophilic impurity, and at least one hydrophilic impurity; (iii) extracting at least one lipophilic impurity from said fermentation broth with a first extractant, whereby (a) a lipophilic-impurity-depleted fermentation broth comprising the at least one rhamnolipid and (b) a first extract comprising said first extractant and said at least one lipophilic impurity are formed; (iv) separating said first extractant and said at least one lipophilic impurity from said first extract; (v) acidulating said lipophilic-impurity-depleted fermentation broth to a pH less than 5, whereby a rhamnolipid-enriched phase is formed; and (vi) separating said rhamnolipid-enriched phase from the acidulated fermentation broth.

A method for the production of a rhamnolipid is also described including (i) obtaining a fermentation broth having a pH greater than 5 and comprising at least one rhamnolipid, at least one lipophilic impurity, and at least one hydrophilic impurity; (ii) extracting at least one lipophilic impurity from said fermentation broth, with a first extractant, whereby (a) a lipophilic-impurity-depleted fermentation broth comprising the at least one rhamnolipid and (b) a first extract comprising said first extractant and said at least one lipophilic impurity are formed; (iii) separating said first extractant and said lipophilic impurity from said first extract; (iv) acidulating said lipophilic-impurity-depleted fermentation broth to a pH less than 5, whereby a rhamnolipid-enriched phase is formed; and (v) separating said rhamnolipid-enriched phase.

A method for the production of a rhamnolipid is also described including (i) obtaining a fermentation broth having a pH greater than 5 and comprising at least one rhamnolipid, at least one lipophilic impurity, and at least one hydrophilic impurity; (ii) acidulating said fermentation broth to a pH less than 5, whereby a hydrophilic-impurity-depleted rhamnolipid-enriched phase is formed; (iii) separating said hydrophilic-impurity-depleted rhamnolipid-enriched phase from said fermentation broth; (iv) dissolving said separated hydrophilic-impurity-depleted rhamnolipid-enriched phase in water and adding a base to form a hydrophilic-impurity-depleted rhamnolipid aqueous solution of pH greater than 5; (v) extracting at least one lipophilic impurity from said hydrophilic-impurity-depleted rhamnolipid aqueous solution with an extractant, whereby a purified rhamnolipid solution and an extract comprising said extractant and said at least one lipophilic impurity are formed; and (vi) separating said extractant and said lipophilic impurity from said extract.

These, and other embodiments are described below.

DETAILED DESCRIPTION OF THE INVENTION

Definitions

As used herein, the term "carbon source" refers to any composition comprising at least one of a carbohydrate composition, a vegetable oil, ethanol, glycerol, methanol, $CO_2$, and CO.

As used herein, the term "nitrogen source" refers to compounds or compositions that may be used to supply an organism with nitrogen during fermentation.

As used herein, the term "extractant" refers to an organic liquid with limited solubility in water, e.g. less than 50% solubility at 25° C. The extractant may be an organic liquid composition comprising one or more components, for example, an oxygenated organic compound and a hydrocarbon. In the case of a multiple-component extractant, each component is referred to as an "extractant component". For example, in case of an extractant comprising an oxygenated organic compound and a hydrocarbon, the oxygenated organic compound and the hydrocarbon may each be referred to as an extractant component.

As used herein, the term "hydrocarbon" refers to any hydrocarbon, including saturated hydrocarbons, unsaturated hydrocarbons, linear hydrocarbons and branched hydrocarbons.

As used herein, the term "oxygenated organic compound" refers to an organic compound comprising at least one oxygen atom, including, e.g. an ether.

Hansen solubility parameter: Solubility parameter (δ) was defined by Hildebrand as the square root of the cohesive energy density, which density is defined as the ratio between heat of vaporization and molar volume of the liquid. Hansen extended the original Hildebrand parameter to a three-dimensional cohesion parameter. According to this concept, the total solubility parameter delta is separated into three different components, or, partial solubility parameters relating to the specific intermolecular interactions:

$$\delta 2 = \delta d^2 + \delta p^2 + \delta h^2$$

wherein δd, δp and δh are the dispersion, polarity, and hydrogen bonding components, respectively. Hoy proposed a system to estimate total and partial solubility parameters. The unit used for those parameters is $MPa^{1/2}$. A detailed explanation of these parameters and components may be found in "CRC Handbook of Solubility Parameters and Other Cohesion Parameters", Allan F. M. Barton, second edition (1991), pages 122-138 which is incorporated by reference herein in its entirety. That and other references provide tables with the parameters for many compounds. In addition, methods for calculating such parameters are provided.

As used herein, "contacting with extractant" "extracting" and "liquid-liquid extraction" interchangeably refer to contacting an aqueous solution or an aqueous slurry with an extractant, whereby a solute in the aqueous solution or slurry transfers (is extracted) to the extractant phase.

As used herein, the term "extract" refers to an extractant-rich phase generated during extraction, which phase comprises said extracted solute.

As used herein, the term "raffinate" refers to the solute-depleted aqueous solution or slurry generated during extraction.

As used herein, the term "extractant to fermentation broth flux ratio" and "flux ratio" interchangeably refer to the ratio between the weight fluxes of the extractant and the fermentation broth.

As used herein, the term "distribution coefficient" refers to the ratio between the concentration of a solute in an organic phase and its concentration in an aqueous phase, while those phases are in equilibrium.

As used herein, the term "selectivity" refers to the ratio between distribution coefficients of two solutes.

As used herein, the term "extraction yield" means the extent of extraction as calculated by dividing the amount of a solute in the extract by the amount of that solute in the extracted solution.

As used herein, the term "vaporizing" refers to transferring from a liquid phase into a vapor phase, e.g. by temperature elevation, pressure reduction, bubbling a gas, or combinations thereof.

As used herein, the term "liquefying" refers to transferring from a vapor phase to a liquid phase, e.g. by temperature reduction, pressure elevation, or combinations thereof.

As used herein, the term "fermentation medium" refers to a composition containing a carbon source (e.g., a carbohydrate), a nitrogen source and optionally other nutrients in which fermentation takes place.

As used herein, the term "fermentation broth" refers to the fermentation medium post fermentation, as such or after removal of biomass therefrom.

As used herein, the term "rhamnolipid" refers to both the protonated and the dissociated forms of the molecule.

As used herein, the term "impurity" refers to any compound other than rhamnolipid, independent of its value and content.

As used herein, the term "lipophilic impurity" refers to any impurity with solubility in hexane of more than 5% at 25° C. Lipophilic impurities are also referred to as "lipophilics". As used herein, the term "lipophilics-depleted" refers to a composition containing a reduced amount or no lipophilics.

As used herein, the term "hydrophilic impurity" refers to any impurity with solubility in water of more than 5% at 25° C. Hydrophilic impurities are also referred to as "hydrophilics". As used herein, the term "hydrophilics-depleted" refers to a composition containing a reduced amount or no hydrophilics.

As used herein, the term "organism capable of producing a rhamnolipid" refers to an organism capable of generating at least 1 g/L rhamnolipid, when cultured in a fermentation medium comprising a carbon source and a nitrogen source.

As used herein, the term "extractant-enriched phase" means a phase comprising extractant at a concentration greater than that in the extract. As used herein, the term "solute-enriched phase" means a phase comprising solute at a concentration greater than that in the extract. In certain embodiments, separating an extractant and solute or extracted compound (rhamnolipid or lipophilic impurity) from an extract may refer to an operation that generates an extractant-enriched phase and a solute-enriched phase.

Unless indicated otherwise, percent is weight percent and ratio is weight ratio. Unless indicated otherwise, weight ratio means the ratio between weight content, e.g. in an aqueous solution containing 20% solute and 80% water, the solute to water weight ratio is 20:80 or 1:4.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

According to an aspect of the invention, provided herein is a method for the production of a rhamnolipid, comprising (i) providing a fermentation medium comprising a carbon source and a nitrogen source; (ii) culturing in said fermentation medium an organism capable of producing a rhamnolipid, wherein said carbon source is metabolized to form a fermentation broth comprising a rhamnolipid, at least one lipophilic impurity, and at least one hydrophilic impurity; (iii) extracting with a first extractant at least one lipophilic impurity from an aqueous solution comprising said rhamnolipid and a lipophilic impurity, which aqueous solution has of pH>5, whereby a first extract comprising said first extractant and said lipophilic impurity is formed; (iv) separating first extractant and lipophilic impurity from said first extract; (v) extracting with a second extractant said rhamnolipid from an aqueous medium comprising said rhamnolipid and hydrophilic impurity, which aqueous medium has of pH<5, whereby a second extract comprising said extractant and purified rhamnolipid is formed; and (vi) separating second extractant and purified rhamnolipid from said second extract.

According to an embodiment, said extracting at least one lipophilic impurity with a first extractant is conducted prior to said extracting rhamnolipid with said second extractant.

According to an embodiment, the method comprises (i) providing fermentation medium comprising a carbon source and a nitrogen source; (ii) culturing in said fermentation medium an organism capable of producing a rhamnolipid, wherein said carbon source is metabolized to form a rhamnolipid in a fermentation broth and wherein the fermentation broth has a pH>5 and comprises at least one lipophilic impurity and at least one hydrophilic impurity; (iii) extracting with a first extractant at least one lipophilic impurity from said fermentation broth, whereby a lipophilics-depleted fermentation broth comprising the rhamnolipid and a first extract comprising said first extractant and said at least one lipophilic impurity are formed; (iv) separating first extractant and lipophilic impurity from said first extract; (v) acidulating said lipophilics-depleted fermentation broth to form acidulated lipophilics-depleted aqueous medium of pH<5 comprising the rhamnolipid; (vi) extracting with a second extractant said rhamnolipid from said acidulated lipophilics-depleted aqueous medium whereby a raffinate and a second extract comprising said second extractant and the rhamnolipid are formed; and (vii) separating second extractant and rhamnolipid from said second extract, whereby a purified rhamnolipid is obtained.

According to an embodiment, said first extractant extracts at least one lipophilic impurity from an aqueous solution comprising said rhamnolipid at least one lipophilic impurity and at least one hydrophilic impurity. According to an embodiment, said aqueous solution is said fermentation broth as such or after modification. According to an embodiment, said modification comprises at least partial removal of cell mass, concentration adjustment (addition or removal of water) and pH adjustment. According to an embodiment, the pH of the aqueous solution to be extracted is greater than 5, greater than 5.5, greater than 6 or greater than 6.5. According to an embodiment, said lipophilic impurity comprises at least one of a triglyceride, mono- and di-glyceride and a fatty acid. According to an embodiment, said hydrophilic impurity comprises at least one of a carbohydrate, an amino acid a mineral anion, a mineral cation and a carboxylic acid.

According to an embodiment, extracting with said first extractant removes from the solution one or more lipophilic impurities, while extracting no rhamnolipid or only a small fraction of it and no or only a little of the hydrophilic impurities. According to an embodiment, said extracting removes from the aqueous solution at least 40%, at least 60%, at least 80% or at least 90% of the lipophilic impurities content.

Said extracting with a first extractant may generate a first extract and a first raffinate. According to an embodiment, said raffinate comprises most or all of the rhamnolipid formed in metabolizing the carbon source, little to no lipophilic impurities, most or all of the hydrophilic impurities in the fermentation broth and optionally an antifoam agent, if used in fermentation. On water-free basis the rhamnolipid in that raffinate is more pure than the rhamnolipid in the broth, which is also referred to as lipophilics-depleted rhamnolipid. According to an embodiment, a fraction of the water co-extracts with lipophilic impurity into the extractant and as a result, the concentration of solutes in the raffinate is greater than that in the fermentation broth. According to an embodiment, the raffinate comprises dissolved extractant, e.g. dissolved oxygenated organic compound.

According to an embodiment, this lipophilics-depleted raffinate of extracting with a first extractant is acidulated, e.g. by adding a mineral acid. According to an embodiment the pH of the raffinate is adjusted to less than 5.5, less than 5.0, less than 4.7, less than 4.3, less than 4.0 or less than 3.6. According to an embodiment, on acidulation the broth becomes turbid. According to an embodiment, the raffinate is turbid and its turbidity increases on acidulation. Said turbidity could be the results of converting the rhamnolipid from its dissociated form to its protonated form. According to an embodiment, the raffinate is enriched with the rhamnolipid by phase separation, e.g. centrifugation or microfiltration, to form a fraction increased in the rhamnolipid (e.g. precipitate or retentate) and a fraction of low rhamnolipid content (e.g. supernatant).

According to an embodiment, the acidulated lipophilics-depleted raffinate or its rhamnolipid-enriched fraction comprise dissolved first extractant and said dissolved extractant is at least partially removed prior to the following step. According to an alternative embodiment, said dissolved extractant is retained.

According to an embodiment, rhamnolipid of the acidulated lipophilics-depleted raffinate or its rhamnolipid-enriched fraction is extracted with said second extractant to form a second raffinate and a second extract comprising said second extractant and purified rhamnolipid. The extraction of the rhamnolipid is selective in that, while the majority of the rhamnolipid is extracted, no or very little of the hydrophilic impurity is extracted. According to an embodiment, the second extract comprises at least 60% of the rhamnolipid in the broth, at least 70%, at least 80%, at least 90% or at least 95%. According to an embodiment, the second extract comprises less than 20% of the hydrophilic impurity in the broth, less than 15%, less than 10%, less than 5% or less than 3%. According to an embodiment, said fermentation broth and said first raffinate also comprise an antifoam agent and extraction is also selective in that no antifoam or just a small fraction of it is extracted along with the rhamnolipid, e.g. less than 30%, less than 20%, less than 15%, less than 10%, less than 5% or less than 3%.

The method further comprises separating the rhamnolipid and the second extractant from the second extract, e.g. by evaporating the second extractant, forming thereby purified rhamnolipid. According to an embodiment, water is co-extracted with the rhamnolipid and on separating from the extract a suspension is formed. According to an embodiment, a purified rhamnolipid-enriched product is formed, e.g. by centrifugation or by microfiltration. According to an embodiment, centrifugation forms a supernatant and a precipitate. According to another embodiment, centrifugation forms three layers—a supernatant and two additional layers both of which comprise purified rhamnolipid. According to another embodiment, those two layers are separated from each other to form two purified rhamnolipid products.

According to an embodiment, extracting rhamnolipid from the acidulated lipophilics-depleted raffinate or from its rhamnolipid-enriched fraction is done in two or more steps forming two or more extracts. According to an embodiment, the same extractant composition is used in each of the steps. According to an alternative embodiment, different extractants are used e.g. differing in the content of the oxygenated organic compound in extractants comprising those compounds and a hydrocarbon. According to an embodiment, extracts of different steps go individually through the separation of rhamnolipid and extractant, forming multiple purified rhamnolipids. According to an embodiment, at least some of the multiple purified rhamnolipids differ in their composition. According to an embodiment, some of the multiple purified rhamnolipids have a greater RRLL/RLL ratio compared with others. According to an embodiment, some of the multiple purified rhamnolipids have a greater proportion of decanoic acid compared with others. According to an embodiment, some of the multiple purified rhamnolipids have a greater purity compared with others.

According to an embodiment, said second raffinate, said supernatant or both are reused, at least partially to provide the fermentation medium, so that rhamnolipid, carbon source and/or nitrogen source present there are not lost. According to another embodiment, said supernatant is recycled to the extraction with the second extractant in order to recovery its rhamnolipid content.

According to an alternative embodiment, said extracting rhamnolipid with said second extractant is conducted prior to said extracting at least one lipophilic impurity with a first extractant.

According to an embodiment, the method comprises (i) providing a fermentation medium comprising a carbon source and a nitrogen source; (ii) culturing in said fermentation medium an organism capable of producing a rhamnolipid, wherein said carbon source is metabolized to form a rhamnolipid in a fermentation broth having a pH>5; (iii) acidulating said fermentation broth to form acidulated aqueous medium of pH<5; (iv) extracting with a second extractant rhamnolipid from said acidulated aqueous medium, whereby a second extract comprising said second extractant and a hydrophilics-depleted rhamnolipid is formed; (v) separating second extractant and hydrophilics-depleted rhamnolipid from said second extract, whereby a separated hydrophilics-depleted rhamnolipid is formed; (vi) adjusting the pH of the separated hydrophilics-depleted rhamnolipid to pH>5; (vii) extracting with a first extractant at least one lipophilic impurity from said separated hydrophilics-depleted pH-adjusted rhamnolipid, whereby an aqueous solution comprising purified rhamnolipid and a first extract comprising said first extractant and said lipophilic impurity are formed; and (vii) separating first extractant and lipophilic impurity from said first extract.

According to an embodiment, said second extractant extracts rhamnolipid from an aqueous solution comprising said rhamnolipid and at least one lipophilic impurity, at least one hydrophilic impurity, and optionally an antifoam agent. According to an embodiment, said aqueous solution is said fermentation broth as such or after modification. According to an embodiment, said modification comprises at least partial removal of cell mass, concentration adjustment (addition or removal of water) and pH adjustment. According to an embodiment, the fermentation broth is acidulated to pH of less than 5.5, less than 5.0, less than 4.7, less than 4.3, less than 4.0 or less than 3.6. According to an embodiment, on acidulation the broth becomes turbid. According to an embodiment, the broth is turbid and its turbidity increases on acidulation. Said turbidity could be the result of converting the rhamnolipid from its dissociated form to its protonated form. According to an embodiment, the method comprises enrichment in rhamnolipid by phase separation, e.g. centrifugation or microfiltration, to form a rhamnolipid-enriched fraction (e.g. precipitate or retentate) and a fraction of low rhamnolipid content (e.g. supernatant).

According to an embodiment, the method further comprises extracting rhamnolipid of the acidulated broth or its rhamnolipid-enriched fraction with said second extractant to form a second raffinate and a second extract comprising said second extractant and purified rhamnolipid. The extraction of the rhamnolipid is selective in that, while the majority of the rhamnolipid is extracted, no or very little of the hydrophilic impurity is extracted. According to an embodiment, the second extract comprises at least 60% of the rhamnolipid in the broth, at least 70%, at least 80%, at least 90% or at least 95%. According to an embodiment, the second extract comprises less than 20% of the hydrophilic impurity in the broth, less than 15%, less than 10%, less than 5% or less than 3%. According to an embodiment, said fermentation broth also comprises an antifoam agent and extraction is also selective in that no antifoam or just a small fraction of it is extracted along with the rhamnolipid, e.g. less than 30%, less than 20%, less than 15%, less than 10%, less than 5% or less than 3%.

The method further comprises separating the rhamnolipid and the second extractant from the second extract, e.g. by evaporating the second extractant, forming thereby a hydrophilics-depleted rhamnolipid. According to an embodiment, water is co-extracted with the rhamnolipid and on separating from the extract a suspension is formed. According to an embodiment, a hydrophilics-depleted rhamnolipid-enriched product is formed, e.g. by centrifugation or by microfiltration. According to an embodiment, centrifugation forms a supernatant and a precipitate. According to another embodiment, centrifugation forms three layers—a supernatant and two additional layers both of which comprising purified rhamnolipid. According to another embodiment, those two layers are separated from each other to form two separated hydrophilics-depleted rhamnolipids.

According to an embodiment, extracting rhamnolipid from the acidulated broth or from its rhamnolipid-enriched fraction is done in two or more steps forming two or more extracts. According to an embodiment, the same extractant composition is used in each of the steps. According to an alternative embodiment, different extractants are used e.g. differing in the content of the oxygenated organic compound in extractants comprising those compounds and a hydrocarbon. According to an embodiment, extracts of different steps go individually through the separation of rhamnolipid and extractant, forming multiple hydrophilics-depleted rhamnolipids. According to an embodiment, at least some of the multiple hydrophilics-depleted rhamnolipids differ in their composition. According to an embodiment, some of the multiple hydrophilics-depleted rhamnolipids have a greater RRLL/RLL ratio compared with others. According to an embodiment, some of the multiple hydrophilics-depleted rhamnolipids have a greater proportion of decanoic acid compared with others. According to an embodiment, some of the multiple hydrophilics-depleted rhamnolipids have a greater purity compared with others.

According to an embodiment, said second raffinate, said supernatant or both are reused, at least partially to provide the fermentation medium, so that rhamnolipid, carbon source and/or nitrogen source present there are not lost. According to another embodiment, said supernatant is recycled to the extraction with the second extractant in order to recovery its rhamnolipid content.

According to an embodiment, the method further comprises adjusting the pH of the separated hydrophilics-depleted rhamnolipid to pH greater than 5, greater than 5.5, greater than 6 or greater than 6.5. According to an embodiment, said pH adjustment generates an aqueous solution comprising said separated hydrophilics-depleted rhamnolipid.

According to an embodiment, said separated hydrophilics-depleted pH-adjusted rhamnolipid solution comprises at least one lipophilic impurity. According to an embodiment, said lipophilic impurity comprises at least one of a triglyceride, mono- and di-glyceride and a fatty acid. According to an embodiment, the method further comprises extracting with a first extractant at least one lipophilic impurity from said separated hydrophilics-depleted pH-adjusted rhamnolipid solution, whereby an aqueous solution comprising purified rhamnolipid and a first extract comprising said first extractant and said lipophilic impurity are formed.

According to an embodiment, extracting with said first extractant removes from the solution one or more lipophilic impurities, while extracting no rhamnolipid or only a small fraction of it. According to an embodiment, said extracting removes from the aqueous solution at least 40%, at least 60%, at least 80% or at least 90% of the lipophilic impurities content. According to an embodiment, said extracting removes from the aqueous solution less than 20% of the rhamnolipid, less than 10%, less than 5%, or less than 3%.

According to an embodiment, said method further comprises a polishing operation for the removal of impurities. According to an embodiment, said polishing operation is selected from the group consisting of contacting with an adsorbent, contacting with active carbon, contacting with an ion-exchanger and combinations thereof. According to an embodiment, said polishing operation comprises contacting with active carbon at least one of said broth, said lipophilics-depleted raffinate, said hydrophilics-depleted rhamnolipid and said purified rhamnolipid.

According to an embodiment, said method comprises acidulating of the lipophilics-depleted raffinate or acidulating of the broth followed by forming a rhamnolipid-comprising precipitate. According to an embodiment, said precipitated is washed with water prior to rhamnolipid extraction with said second extractant in order to further remove hydrophilic impurities.

According to an embodiment, the purified rhamnolipid has rhamnolipid to lipophilic impurity weight/weight ratio that is at least 3 times greater than that ratio in the fermentation broth, at least 5 times greater, at least 10 times greater, at least 15 times greater, at least 20 times greater, at least 25 times greater or at least 30 times greater. According to an embodiment, the purified rhamnolipid has rhamnolipid to hydrophilic impurity weight/weight ratio that is at least 3 times greater than that ratio in the fermentation broth, at least 5 times greater, at least 10 times greater, at least 15 times greater, at least 20 times greater, at least 25 times greater or at least 30 times greater. According to an embodiment, the purified rhamnolipid has rhamnolipid to antifoam agent weight/weight ratio that is at least 3 times greater than that ratio in the fermentation broth, at least 5 times greater, at least 10 times greater, at least 15 times greater, at least 20 times greater, at least 25 times greater or at least 30 times greater.

According to an embodiment, compared on the same rhamnolipid concentration and same test parameters said purified rhamnolipid has foaming capability that is at least 3 times greater than that of the rhamnolipid in the fermentation broth, at least 5 times greater, at least 10 times greater, at least 15 times greater, at least 20 times greater, at least 25 times greater or at least 30 times greater.

According to an embodiment, a solution of said purified rhamnolipid is of lighter color than the fermentation broth having the same rhamnolipid concentration. According to an embodiment, the solution of said purified rhamnolipid has no color or is light yellow.

According to an embodiment, said purified rhamnolipid is in the form of solid or an aqueous dispersion, as formed on separation from the extract formed on extracting the rhamnolipid from the lipophilics-depleted broth or on acidulation of the purified rhamnolipid formed on extracting lipophilics impurities from hydrophilics-depleted rhamnolipid. According to another embodiment, said purified rhamnolipid is in the form of an aqueous solution of pH>5, as formed on extracting lipophilic impurities from hydrophilics-depleted rhamnolipid or on dissolving in a basic solution the purified rhamnolipid separated from the extract formed on rhamnolipid extraction from lipophilics-depleted broth. According to an embodiment, on dissolving in basic solution the purified rhamnolipid separated from the extract in a basic solution, the amount of basic solution used is adjusted to generate a solution of desired rhamnolipid concentration. According to an embodiment, said purified rhamnolipid is in the form of an aqueous solution comprising about 5% rhamnolipid, about 10%, about 20%, about 30%, about 40%, or about 50%.

Any carbon source is suitable for the fermentation medium. According to an embodiment, said carbon source is selected from the group consisting of carbohydrates, sugar alcohols, glycerol and vegetable oils. According to an embodiment, said carbon source comprises a triglyceride.

According to an embodiment, said organism capable of producing a rhamnolipid is selected from the group consisting of *Pseudomonas aeruginosa*, *Pseudomonas chlororaphis*, *Pseudomonas putida*, other rhamnolipid-producing *Pseudomonas* strains, *Burkholderia mallei*, *Burkholderia pseudomallei*, *Burkholderia thailandensis*, other rhamnolipid-producing *Burkholderia* strains, *Acinetobacter calcoaceticus*, *Enterobacter asburiae*, *Enterobacter hormaechei*, *Pantoea stewartii*, *Thermus aquaticus*, *Meiothermus ruber*, and *Tetragenococcus koreensis*.

According to an embodiment, said rhamnolipid is selected from RLL, RRLL and combinations thereof. As used herein RLL denotes a rhamnolipid composed of two fatty acids and a single rhamnose sugar moiety. As used herein RRLL denotes a rhamnolipid composed of two fatty acids and a two rhamnose sugar moieties. According to an embodiment, said fatty acid is beta-hydroxy-decanoic acid. According to an embodiment, said rhamnolipid is selected from alpha-L-rhamnopyranosyl-beta-hydroxydecanoyl-beta-hydroxydecanoate, 2-alpha-L-rhamnopyranosyl-alpha-L-rhamnopyranosyl-beta-hydroxydecanoyl-beta-hydroxydecanoate and combinations thereof.

According to an embodiment, rhamnolipid concentration in said fermentation broth may be in the range between 1 g/L and 50 g/L, between 5 g/L and 40 g/L or between 15 g/L and 35 g/L.

According to an embodiment, said first extractant, said second extractant or both comprise at least one of a hydrocarbon having a boiling point under 20° C. while at atmospheric pressure, and an oxygenated organic compound having a boiling point under 20° C. while at atmospheric pressure, wherein said oxygenated organic compound is characterized by Hansen solubility parameter polarity component in the range between 2 MPa$^{0.5}$ and 8 MPa$^{0.5}$; and Hansen solubility parameter H-bond component in the range between 2 MPa$^{0.5}$ and 8 MPa$^{0.5}$.

According to an embodiment, the boiling point of said hydrocarbon at atmospheric pressure is under 20° C., under 15° C., under 10° C., or under 5° C.

According to an embodiment, the Hansen solubility parameter polarity component of said oxygenated organic compound is in the range between 2 MPa$^{0.5}$ and 8 MPa$^{0.5}$, between 3 MPa$^{0.5}$ and 7 MPa$^{0.5}$, between 4 MPa$^{0.5}$ and 6 MPa$^{0.5}$. According to an embodiment, the Hansen solubility parameter H-bond component of said oxygenated organic compound is in the range between 2 MPa$^{0.5}$ and 8 MPa$^{0.5}$, between 3 MPa$^{0.5}$ and 7 MPa$^{0.5}$, between 4 MPa$^{0.5}$ and 6 MPa$^{0.5}$.

According to an embodiment, both said first extractant and said second extractant comprise at least one of said hydrocarbon and said oxygenated organic compound.

According to an embodiment, said hydrocarbon is selected from the group consisting of $C_3$-$C_5$ alkanes, $C_3$-$C_5$ alkenes, and combinations thereof. According to an embodiment, said hydrocarbon is an olefin. According to an embodiment, said olefin is selected from the group consisting of propene, 1-butene, 2-butene and iso-butene.

According to an embodiment, said oxygenated organic compound is selected from the group consisting of dimethyl ether, methyl-ethyl ether, diethyl ether and combinations thereof. According to an embodiment, said oxygenated compound is dimethyl ether.

According to an embodiment, said first extractant, said second extractant or both comprise both said oxygenated organic compound and an olefin having a boiling point under 20° C. while at atmospheric pressure. According to an embodiment, said first extractant, said second extractant or both comprise both said oxygenated organic compound and an olefin having a boiling point under 20° C. while at atmospheric pressure, at an oxygenated organic compound/olefin weight/weight ratio between 1:10 and 10:1, between 1:8 to 8:1, between 1:6 to 6:1 or between 1:4 to 4:1. According to an embodiment, said first extractant, said second extractant or both comprise a butene and dimethylether.

According to an embodiment, said first extractant and said second extractant are of the same composition. According to an alternative embodiment, said first extractant comprises an olefin and said second extractant comprises said oxygenated organic compound.

According to an embodiment, separating the first extractant and lipophilic impurity from said first extract, separating the second extractant and purified rhamnolipid from said second extract, or both, comprises evaporating said extractant, e.g. by pressure reduction, by temperature elevation or both.

According to an embodiment, said extracting a lipophilic impurity with a first extractant forms a first raffinate beside said first extract and said first raffinate comprises said first extractant. According to an embodiment, said extracting a rhamnolipid with a second extractant forms a second raffinate beside said second extract and said second raffinate comprises said second extractant. According to an embodiment, the method further comprises separating first extractant from said raffinate, separating second extractant from said second raffinate or both. According to an embodiment, said separating comprises evaporating said extractant, e.g. by pressure reduction, by temperature elevation or both.

According to an embodiment, said separating said first extractant from said first extract, from said first raffinate or both results in first extractant in a vapor phase. According to an embodiment, said separating said second extractant from said second extract, from said second raffinate or both results in second extractant in a vapor phase. According to an embodiment, said method further comprises liquefying at least a fraction of said vapor phase first extractant, liquefying at least a fraction of said vapor phase second extractant or both. According to an embodiment, said liquefying is driven by a refrigerant circuit. According to an embodiment, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

According to an embodiment, further provided is purified rhamnolipid produced according to said method.

According to an embodiment, further provided is a commercial product comprising purified rhamnolipid produced according to said method. According to an embodiment, said commercial product is selected from the group comprising cosmetics, food and drilling aids.

According to another aspect of the invention, provided herein is a method for the production of rhamnolipid which comprises (i) providing fermentation medium comprising a carbon source and a nitrogen source; (ii) culturing in said fermentation medium an organism capable of producing a rhamnolipid, wherein said carbon source is metabolized to form a fermentation broth having a pH>5 and comprising a rhamnolipid, at least one lipophilic impurity, and at least one hydrophilic impurity; (iii) acidulating said fermentation brothto form an acidulated aqueous medium of pH<5; (iv) extracting that at least one rhamnolipid from said acidulated aqueous medium with a first extractant to remove the at least one hydrophilic impurity, thereby obtaining a first extract comprising the at least one rhamnolipid and the first extractant; (v) separating the first extractant and the at least one rhamnolipid from said first extract to obtain a separated rhahmnolipid medium; (vi) adjusting the pH of the separated rhamnolipid medium to pH>5; and (viii) extracting the at least one lipophilic impurity from said pH-adjusted rhamnolipid medium with a second extractant to obtain an aqueous solution comprising purified rhamnolipid.

In an alternative embodiment, provided herein is a method for the production of a rhamnolipid, comprising (i) providing a fermentation medium comprising a carbon source and a nitrogen source; (ii) culturing in said fermentation medium an organism capable of producing a rhamnolipid, wherein said carbon source is metabolized to form a fermentation broth comprising a rhamnolipid, at least one lipophilic impurity, and at least one hydrophilic impurity; (iii) extracting with a first extractant at least one lipophilic impurity from an aqueous solution comprising said rhamnolipid and a lipophilic impurity, which aqueous solution has a pH>5, whereby a raffinate and a first extract comprising said extractant and said lipophilic impurity are formed; (iv) separating first extractant and lipophilic impurity from said first extract; (v) acidulating said fermentation broth to a pH<5, whereby a rhamnolipid-enriched phase is formed; and (vi) separating said rhamnolipid-enriched phase.

According to an embodiment, said extracting at least one lipophilic impurity with a first extractant is conducted prior to said acidulating and forming a rhamnolipid-enriched phase.

According to an embodiment, said first extractant extracts at least one lipophilic impurity from an aqueous solution comprising said rhamnolipid, at least one lipophilic impurity, and at least one hydrophilic impurity. According to an embodiment, said aqueous solution is said fermentation broth as such or after modification. According to an embodiment, said modification comprises at least partial removal of cell mass, concentration adjustment (addition or removal of water) and pH adjustment. According to an embodiment, the pH of the aqueous solution to be extracted is greater than 5, greater than 5.5, greater than 6 or greater than 6.5. According to an embodiment, said lipophilic impurity comprises at least one of a triglyceride, mono- and di-glyceride and a fatty acid. According to an embodiment, said hydrophilic impurity comprises at least one of a carbohydrate, an amino acid a mineral anion, a mineral cation and a carboxylic acid.

According to an embodiment, extracting with said first extractant removes from the solution one or more lipophilic impurities, while extracting no rhamnolipid or only a small fraction of it and no or only a little of the hydrophilic impurities. According to an embodiment, said extracting removes from the aqueous solution at least 40%, at least 60%, at least 80% or at least 90% of the lipophilic impurities content. According to an embodiment, said extracting removes from the aqueous solution less than 20% of the rhamnolipid, less than 10%, less than 5%, or less than 3%.

Said extracting with a first extractant may generate a first extract and a first raffinate. According to an embodiment, said raffinate comprises most or all of the rhamnolipid formed in metabolizing the carbon source, little to no lipophilic impurities, most or all of the hydrophilic impurities in the fermentation broth and optionally an antifoam agent, if used in fermentation. On water-free basis the rhamnolipid in that raffinate is more pure than the rhamnolipid in the broth, which is also referred to as lipophilics-depleted rhamnolipid. According to an embodiment, a fraction of the water co-extracts with lipophilic impurity into the extractant and as a result, the concentration of solutes in the raffinate is greater than that in the fermentation broth. According to an embodiment, the raffinate comprises dissolved extractant, e.g. dissolved oxygenated organic compound.

According to an embodiment, this lipophilics-depleted raffinate of extracting with a first extractant is acidulated, e.g. by adding a mineral acid. According to an embodiment the pH of the raffinate is adjusted to less than 5.5, less than 5.0, less than 4.7, less than 4.3, less than 4.0 or less than 3.6. According to an embodiment, on acidulation, a rhamnolipid-enriched phase is formed. According to an embodiment said rhamnolipid-enriched phase forms turbidity or suspension in said acidulated lipophilics-depleted raffinate.

Said turbidity could be the results of converting the rhamnolipid from its dissociated form to its protonated form. According to an embodiment, the acidulated lipophilics-depleted raffinate comprise dissolved first extractant and said dissolved extractant is at least partially removed prior to the following step.

According to an embodiment, the method further comprises separating said rhamnolipid-enriched phase. According to an embodiment, said separating comprises at least one of centrifugation and microfiltration. According to an embodiment, said separating said rhamnolipid-enriched phase further forms a supernatant. According to an embodiment, said separating comprises centrifugation and said centrifugation forms three layers—a supernatant and two additional layers both of which comprising purified rhamnolipid. According to another embodiment, those two layers are separated from each other to form two purified rhamnolipid products.

According to an embodiment, said acidulating and forming rhamnolipid-enriched phase is conducted prior to said extracting at least one lipophilic impurity with a first extractant.

According to an embodiment, said method comprises (i) providing a fermentation medium comprising a carbon source and a nitrogen source; (ii) culturing in said fermentation medium an organism capable of producing a rhamnolipid, wherein said carbon source is metabolized to form a fermentation broth comprising a rhamnolipid, and wherein the fermentation broth has a pH>5; (iii) acidulating said fermentation broth to a pH<5, whereby a hydrophilics-depleted rhamnolipid-enriched phase is formed; (iv) separating said hydrophilics-depleted rhamnolipid-enriched phase; (v) dissolving said rhamnolipid-enriched phase in water to form a hydrophilics-depleted rhamnolipid aqueous solution of pH>5; (vi) extracting a lipophilic impurity from said hydrophilics-depleted rhamnolipid aqueous solution with a first extractant, whereby a purified rhamnolipid solution and a first extract comprising said extractant and said lipophilic impurity are formed; and (vii) separating first extractant and lipophilic impurity from said first extract.

According to an embodiment, the method comprises separating a rhamnolipid-enriched phase from an acidulated solution comprising said rhamnolipid at least one lipophilic impurity and at least one hydrophilic impurity. According to an embodiment, said aqueous solution is said fermentation broth as such or after modification. According to an embodiment, said modification comprises at least partial removal of cell mass, concentration adjustment (addition or removal of water) and pH adjustment. According to an embodiment, the pH of the aqueous solution comprises acidulation, e.g. by adding a mineral acid. According to an embodiment the pH of the fermentation broth is adjusted to less than 5.5, less than 5.0, less than 4.7, less than 4.3, less than 4.0 or less than 3.6.

According to an embodiment, on acidulation, a rhamnolipid-enriched phase is formed. According to an embodiment said rhamnolipid-enriched phase forms turbidity or suspension in said acidulated broth. According to an embodiment said suspended rhamnolipid-enriched phase is solid or liquid (depending, among others on the temperature). Said turbidity could be the results of converting the rhamnolipid from its dissociated form to its protonated form. According to an embodiment, said rhamnolipid-enriched phase is suspended in the aqueous medium of the broth. Hence, that aqueous medium gets depleted in rhamnolipid and the suspended phase is enriched in the rhamnolipid. According to an embodiment, hydrophilic impurities do not enter the rhamnolipid-enriched phase and stay in the aqueous phase, so that that rhamnolipid-enriched phase is depleted in hydrophilic impurities. According to an embodiment, said broth comprises an antifoam agent and said agent also stays in the aqueous solution, so that said rhamnolipid-enriched phase is depleted in both hydrophilic impurities and antifoam agent.

According to an embodiment, the method further comprises separating said hydrophilics-depleted rhamnolipid-enriched phase. According to an embodiment, said separating comprises at least one of centrifugation and microfiltration. According to an embodiment, said separating said hydrophilics-depleted rhamnolipid-enriched phase further forms a supernatant. According to an embodiment, said separating comprises centrifugation and said centrifugation forms three layers—a supernatant and two additional layers both of which comprising hydrophilics-depleted rhamnolipid. According to another embodiment, those two layers are separated from each other to form two hydrophilics-depleted rhamnolipid products.

According to an embodiment, the method comprises dissolving said separated hydrophilics-depleted rhamnolipid-enriched phase in water to form a hydrophilics-depleted rhamnolipid aqueous solution of pH>5 and extracting a lipophilic impurity from said hydrophilics-depleted rhamnolipid aqueous solution with a first extractant, whereby a purified rhamnolipid solution and a first extract comprising said extractant and said lipophilic impurity are formed. According to an embodiment, dissolving said separated hydrophilics-depleted rhamnolipid-enriched phase in water comprise dissolving in basic water, wherein the base amount is such that the desired pH is reached. According to an embodiment, the pH of said hydrophilics-depleted rhamnolipid aqueous solution is greater than 5, greater than 5.5, greater than 6 or greater than 6.5.

According to an embodiment, hydrophilics-depleted rhamnolipid aqueous solution comprises at least one lipophilic impurity. According to an embodiment, said lipophilic impurity comprises at least one of a triglyceride, mono- and di-glyceride and a fatty acid.

According to an embodiment, said extracting with said first extractant removes from hydrophilics-depleted rhamnolipid aqueous solution one or more lipophilic impurities, while extracting no rhamnolipid or only a small fraction of it. According to an embodiment, said extracting removes from the aqueous solution at least 40%, at least 60%, at least 80% or at least 90% of the lipophilic impurities content. According to an embodiment, said extracting removes from the aqueous solution less than 20% of the rhamnolipid, less than 10%, less than 5%, or less than 3%.

Said extracting with a first extractant generates a first extract and a first raffinate. According to an embodiment, said raffinate comprises most or all of the rhamnolipid formed in metabolizing the carbon source in a purified form. According to an embodiment, a fraction of the water co-extracts with lipophilic impurity into the extractant and as a result, the concentration of rhamnolipid in the raffinate is greater than that in the hydrophilics-depleted rhamnolipid aqueous solution. According to an embodiment, the raffinate comprises dissolved extractant, e.g. dissolved oxygenated organic compound, and that dissolved extractant is removed by evaporation.

According to an embodiment, said supernatant is reused, at least partially to provide the fermentation medium, so that rhamnolipid, carbon source and/or nitrogen source present there are not lost.

According to an embodiment, said method further comprises a polishing operation for the removal of impurities. According to an embodiment, said polishing operation is selected from the group consisting of contacting with an adsorbent, contacting with active carbon, contacting with an ion-exchanger and combinations thereof. According to an embodiment, said polishing operation comprises contacting with active carbon at least one of said broth, said lipophilics-depleted raffinate, said hydrophilics-depleted rhamnolipid and said purified rhamnolipid.

According to an embodiment, said rhamnolipid-enriched phase (formed on acidulating said broth or on acidulating said lipophilics-depleted raffinate) is washed with water in order to further remove hydrophilic impurities.

According to an embodiment, the purified rhamnolipid has a rhamnolipid to lipophilic impurity weight/weight ratio that is at least 3 times greater than that ratio in the fermentation broth, at least 5 times greater, at least 10 times greater, at least 15 times greater, at least 20 times greater, at least 25 times greater or at least 30 times greater. According to an embodiment, the purified rhamnolipid has a rhamnolipid to hydrophilic impurity weight/weight ratio that is at least 3 times greater than that ratio in the fermentation broth, at least 5 times greater, at least 10 times greater, at least 15 times greater, at least 20 times greater, at least 25 times greater or at least 30 times greater. According to an embodiment, the purified rhamnolipid has a rhamnolipid to antifoam agent weight/weight ratio that is at least 3 times greater than that ratio in the fermentation broth, at least 5 times greater, at least 10 times greater, at least 15 times greater, at least 20 times greater, at least 25 times greater or at least 30 times greater.

According to an embodiment, compared on the same rhamnolipid concentration and same test parameters said purified rhamnolipid has foaming capability that is at least 3 times greater than that of the rhamnolipid in the fermentation broth, at least 5 times greater, at least 10 times greater, at least 15 times greater, at least 20 times greater, at least 25 times greater or at least 30 times greater.

According to an embodiment, compared on the same rhamnolipid concentration a solution of said purified rhamnolipid is of lighter color than the fermentation broth. According to an embodiment, the solution of said purified rhamnolipid has no color or is light yellow.

According to an embodiment, said purified rhamnolipid is in the form of solid or an aqueous dispersion, as formed on acidulation. According to another embodiment, said purified rhamnolipid is in the form of an aqueous solution of pH>5, as formed on dissolving in a basic solution said rhamnolipids enriched phase. According to an embodiment, on dissolving in basic solution the purified rhamnolipid separated from the extract in a basic solution, the amount of basic solution used is adjusted to generate a solution of desired rhamnolipid concentration. According to an embodiment, said purified rhamnolipid is in the form of an aqueous solution comprising about 5% rhamnolipid, about 10%, about 20%, about 30%, about 40%, or about 50%.

Any carbon source is suitable for the fermentation medium. According to an embodiment, said carbon source is selected from the group consisting of carbohydrates, sugar alcohols, glycerol and vegetable oils. According to an embodiment, said carbon source comprises a triglyceride.

According to an embodiment, said organism capable of producing a rhamnolipid is selected from the group consisting of *Pseudomonas aeruginosa, Pseudomonas chlororaphis, Pseudomonas putida*, other rhamnolipid-producing *Pseudomonas* strains, *Burkholderia mallei, Burkholderia pseudomallei, Burkholderia thailandensis*, other rhamnolipid-producing *Burkholderia* strains, *Acinetobacter calcoaceticus, Enterobacter asburiae, Enterobacter hormaechei, Pantoea stewartii, Thermus aquaticus, Meiothermus ruber*, and *Tetragenococcus koreensis*.

According to an embodiment, said rhamnolipid is selected from RLL, RRLL and combinations thereof. As used herein RLL denotes a rhamnolipid composed of two fatty acids and a single rhamnose sugar moiety. As used herein RRLL denotes a rhamnolipid composed of two fatty acids and two rhamnose sugar moieties. According to an embodiment, said fatty acid is beta-hydroxy-decanoic acid. According to an embodiment, said rhamnolipid is selected from alpha-L-rhamnopyranosyl-beta-hydroxydecanoyl-beta-hydroxydecanoate, 2-alpha-L-rhamnopyranosyl-alpha-L-rhamnopyranosyl-beta-hydroxydecanoyl-beta-hydroxydecanoate and combinations thereof.

According to an embodiment, rhamnolipid concentration in said fermentation broth is in the range between 1 g/L and 50 g/L, between 5 g/L and 40 g/L or between 15 g/L and 35 g/L.

According to an embodiment, said first extractant comprises at least one of a hydrocarbon having a boiling point under 20° C. while at atmospheric pressure, and an oxygenated organic compound having a boiling point under 20° C. while at atmospheric pressure, wherein said oxygenated organic compound is characterized by Hansen solubility parameter polarity component in the range between 2 $MPa^{0.5}$ and 8 $MPa^{0.5}$; and Hansen solubility parameter H-bond component in the range between 2 $MPa^{0.5}$ and 8 $MPa^{0.5}$.

According to an embodiment, the boiling point of said hydrocarbon at atmospheric pressure is under 20° C., under 15° C., under 10° C., or under 5° C.

According to an embodiment, the Hansen solubility parameter polarity component of said oxygenated organic compound is in the range between 2 $MPa^{0.5}$ and 8 $MPa^{0.5}$, between 3 $MPa^{0.5}$ and 7 $MPa^{0.5}$, between 4 $MPa^{0.5}$ and 6 $MPa^{0.5}$. According to an embodiment, the Hansen solubility parameter H-bond component of said oxygenated organic compound is in the range between 2 $MPa^5$ and 8 $MPa^{0.5}$, between 3 $MPa^{0.5}$ and 7 $MPa^{0.5}$, between 4 $MPa^{0.5}$ and 6 $MPa^{0.5}$.

According to an embodiment, said first extractant comprises at least one of said hydrocarbon and said oxygenated organic compound.

According to an embodiment, said hydrocarbon is selected from the group consisting of $C_3$-$C_5$ alkanes, $C_3$-$C_5$ alkenes, and combinations thereof. According to an embodiment, said hydrocarbon is an olefin. According to an embodiment, said olefin is selected from the group consisting of propene, 1-butene, 2-butene and iso-butene.

According to an embodiment, said oxygenated compound is selected from the group consisting of dimethyl ether, methyl-ethyl ether, diethyl ether and combinations thereof. According to an embodiment, said oxygenated compound is dimethyl ether.

According to an embodiment, said first extractant comprises both said oxygenated organic compound and an olefin having a boiling point under 20° C. while at atmospheric pressure. According to an embodiment, said first extractant comprises both said oxygenated organic compound and an olefin having a boiling point under 20° C. while at atmospheric pressure, at an oxygenated organic compound/olefin weight/weight ratio between 1:10 and 10:1, between 1:8 to 8:1, between 1:6 to 6:1 or between 1:4 to 4:1. According to an embodiment, said first extractant comprises a butene and dimethylether.

According to an embodiment, said separating first extractant and lipophilic impurity from said first extract comprises evaporating said extractant, e.g. by pressure reduction, by temperature elevation or both.

According to an embodiment, said extracting a lipophilic impurity with a first extractant forms a first raffinate beside said first extract and said first raffinate comprises said first extractant. According to an embodiment, the method further comprises separating first extractant from said raffinate. According to an embodiment, said separating comprises evaporating said extractant, e.g. by pressure reduction, by temperature elevation or both.

According to an embodiment, said separating said first extractant results in first extractant in a vapor phase. According to an embodiment, said method further comprises liquefying at least a fraction of said vapor phase first extractant.

According to an embodiment, said liquefying is driven by a refrigerant circuit. According to an embodiment, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

According to an embodiment, further provided is purified rhamnolipid produced according to said method.

According to an embodiment, further provided is a commercial product comprising purified rhamnolipid produced according to said method. According to an embodiment, said commercial product is selected from the group comprising cosmetics, food and drilling aids.

Exemplary Extraction Embodiments

The method of the first aspect may comprise extracting an aqueous solution comprising a rhamnolipid, e.g. fermentation broth as is or after modification, e.g. removal of a lipophilic compound, with an extractant to form an extract and a raffinate, wherein both extract and raffinate comprise said extractant, water and optionally a rhamnolipid.

According to an embodiment, said extractant comprises an oxygenated organic compound and a hydrocarbon and said hydrocarbon and said oxygenated organic compound together form at least about 80% of said extractant, at least 85%, at least 90%, at least 95%, or at least 99%. According to an embodiment, said extractant further comprises minor amounts (e.g. less than 2% or less than 1%) of water. According to an embodiment, the weight ratio between said oxygenated organic compound and said hydrocarbon in said extractant is in the range between about 1 and about 0.01, between 0.9 and 0.05, between 0.85 and 0.1 or between 0.8 and 0.15. According to an embodiment, said hydrocarbon forms at least about 50% of said extractant, at least 60%, at least 70%, at least 80% or at least 90%. According to an embodiment, said oxygenated organic compound forms at least about 5% of said extractant, at least 10%, at least 15%, at least 20% or at least 25%.

According to an embodiment, said extractant composition is selected so that on equilibrating 100 g of extractant with 10 g of water at 25° C. and 5 bar, the concentration of said oxygenated organic compound in the water is less than 10%, less than 8% or less than 6%.

According to an embodiment, said extracted fermentation broth comprises cell mass. According to this embodiment, cell mass is present in the fermentation broth during extraction.

According to an embodiment, said extracting is conducted at a temperature between about 20° C. and about 50° C., between about 25° C. and about 45° C. or between about 30° C. and about 40° C. In various embodiments, extracting is conducted at about fermentation temperature. According to an embodiment, extraction is conducted in an extraction column and the temperature changes along the column.

In various embodiments, extracting is conducted at pressure between about 1.5 bar and about 10 bar, between about 2 bar and about 9 bar or between about 3 bar and about 8 bar.

According to an embodiment, extracting comprises mixing said aqueous solution with said extractant, followed by separating the generated extractant-rich phase (extract, typically the lighter phase) from the generated water-rich phase (raffinate, typically the heavier phase). Any form of mixing is suitable. Any form of phase separation is suitable. According to an embodiment, said extracting comprises multiple steps, e.g. between 2 and 30 stages, between 2 and 20 stages or between 2 and 10 stages. According to an embodiment, extracting is conducted counter-currently, also referred to as extracting in a counter-current mode. According to an embodiment, extracting is conducted in a series of mixer settlers, in an extraction column or in a centrifugal contactor.

According to varying embodiments, the flux ratio of extractant to broth is in the range of from about 0.1 to about 20, from about 0.3 to about 10, from about 0.4 to about 8, or from about 0.5 to about 3.

Methods for performing liquid-liquid extraction ("LLE") in a countercurrent column have been well documented in the literature, e.g., by Treybal, Robert E., "Liquid Extraction," McGraw-Hill, New York, 1951), which document is incorporated by reference herein in its entirety. Each countercurrent stage can be implemented with a mixer and settler. As an integrated system with multiple stages, a spray tower may be used (e.g., per FIG. 10.1 in Treybal). In addition, conventional tray columns using disk and donut baffles find use (FIG. 10.4a and 10.4b in Treybal). Further, a column with random packing and flow distributor regions, using packing such as raschig rings, PALL Rings, INTALOX saddles, or berl saddles, find use. In addition, a Podbielniak extractor could optionally be used (FIG. 10.12 in Treybal). Such devices are also described, e.g., in Perry's Chemical Engineering Handbook (Chapter 15, 8th edition, 2008). Columns that find use in the present extraction methods include static extraction columns, agitated extraction columns, mixer-settlers, or centrifugal extractors. Any one of these configurations can be configured to implement the desired number of stages. Economics, as constrained by throughput and equipment space constraints, would define the preferred configuration. An illustrative multistage centrifugal extractor is available from Robatel, Inc. (on the internet at rousselet-robatel.com/products/multistage-centrif-extractors-lx.php). Use of centrifugal countercurrent columns for continuous LLE is also described, e.g., on the internet at cheresources.com/centcontactor.shtml.

According to an embodiment, during extracting lipophilic impurity from a neutral aqueous solution comprising a rhamnolipid and a lipophilic impurity, the distribution coefficient of the lipophilic impurity is at least 0.5, at least 0.7, at least 0.9, at least 1.1, at least 1.3, at least 1.5, at least 1.7, at least 2.0, at least 2.5, or at least 3.0 and the distribution coefficient of the rhamnolipid is less than 1.0, less than 0.8, less than 0.6, less than 0.4, less than 0.2, less than 0.1, or less than 0.05. According to an embodiment, during extracting a rhamnolipid from an acidic aqueous solution comprising said rhamnolipid, the distribution coefficient of the rhamnolipid is at least 0.5, at least 0.7, at least 0.9, at least 1.1, at least 1.3, at least 1.5, at least 1.7, at least 2.0, at least 2.5, or at least 3.0

According to an embodiment, said rhamnolipid is extracted from acidic aqueous solution selectively over water, i.e. the ratio between rhamnolipid distribution coefficient and water distribution coefficient is greater than 1, e.g. at least 1.5, at least 2, at least 2.5, at least 3, at least 3.5, at least 4, at least 5, at least 7 or at least 10.

EXAMPLES

Methods

A fermentation broth was received. It contained 1.12% wt rhamnolipids, was of pH 6.8 and had a brown color. The biomass was removed by filtering on an EMD Millipore microfiltration membrane. Acidulation, where conducted, used sulfuric acid of about 1M.

Extraction was conducted in a shake vessel consisting of a glass pressure tube, a pressure gauge, and a stainless steel metering valve. First the filtered broth was added to the vessel and then an extractant was added. Mixing was applied for a time long enough to ensure reaching equilibrium. Then, the vessel was kept for time sufficiently long for complete phase separation, whereby two clear phases were observed. The raffinate was removed first by opening the metering valve. In order to remove the extract, a lock fitting with a needle was installed, and the extract was drained into a serum bottle. This was done to assure a slow degassing process. Once all of the material is sufficiently degassed, samples of the feeds, raffinates, and extracts were prepared for analysis. The analysis was done via a spectrophotometric assay, where the sample was blended with an orcinol solution and heated to 80° C.

Example 1

Lipophilic Impurity Extraction from Fermentation Liquor using Dimethyl Ether (DME) as the Extractant 46.61 gr filtered broth was extracted with 39.91 gr DME. 69.05 gr raffinate and 17.18 gr extract were formed. The raffinate and extract were allowed to degas, resulting in 42.94 gr of degassed raffinate and 1.24 gr of degassed extract. Rhamnolipid concentration in the degassed raffinate was 0.80 wt %. The degassed extract was centrifuged and two phases were observed—1.21 gr supernatant and 0.03 gr precipitate Rhamnolipid concentration in the supernatant and in the precipitate were 1.30 wt %, and 6.46 wt %, respectively. Distribution coefficient (DC) for rhamnolipids distribution between the phases (rhamnolipids concentration in the extract before degassing divided by rhamnolipids concentration in the raffinate before degassing) was 0.21.

Example 2

Lipophilic Impurity Extraction from Fermentation Liquor Using 1-Butene as the Extractant 38.14 gr filtered broth was extracted with 39.84 gr 1-butene. 37.25 gr raffinate and 39.25 gr extract were formed. The raffinate and extract were allowed to degas, resulting in 36.37 gr of degassed raffinate and 0.41 gr of degassed extract Rhamnolipid concentration in the degassed raffinate was 1.13 wt %. The degassed extract was centrifuged and two phases were observed—0.40 gr supernatant and 0.01 gr precipitate Rhamnolipid concentration in the supernatant and in the precipitate were 0.33 wt %, and 21.9 wt %, respectively Rhamnolipids DC was 0.01.

These results of Examples 1 and 2 demonstrate that the majority of the rhamnolipid stay in the raffinate when extracting the broth at about neutral pH. When using 1-butene as the extractant, extraction of rhamnolipid is negligible. The samples were not analyzed for lipophilic impurities, but it is assumed that those are efficiently extracted at the neutral pH, as demonstrated by the high purity of the products in Examples 3 and 4 and by the efficient foaming in Example 5 below.

Example 3

Rhamnolipids Extraction from Acidulated Lipophilics-Depleted Fermentation Liquor of Example 1, Using DME as the Extractant The raffinate formed in Example 1 (DME extraction) was acidulated to pH of 3.50.

41.41 g of the acidulated raffinate was extracted with 42.92 gr DME. 38.56 gr raffinate and 43.87 gr extract were formed. The raffinate and extract were allowed to degas, resulting in 25.26 gr of degassed raffinate and 15.86 gr of degassed extract Rhamnolipid concentration in the degassed raffinate was 0.20 wt %. The degassed extract was centrifuged and three phases were observed–15.55 gr supernatant, 0.29 gr of an intermediate phase (gel like) and 0.02 gr precipitate Rhamnolipid concentration in the supernatant and in the heavy phases (combined gel-like intermediate phase+precipitate) were 0.08% wt and >90% wt %, respectively. Rhamnolipids DC was 9.31.

Example 4

Rhamnolipids Extraction from Acidulated Lipophilics-Depleted Fermentation Liquor of Example 2, Using DME as the Extractant The raffinate formed in Example 2 (1-butene extraction) was acidulated to pH of 3.42.

35.98 gr of the acidulated raffinate was extracted with 43.40 gr DME. 50.94 gr raffinate and 27.88 gr extract were formed. The raffinate and extract were allowed to degas, resulting in 32.37 gr of degassed raffinate and 2.33 gr of degassed extract Rhamnolipid concentration in the degassed raffinate was 0.21 wt %. The degassed extract was centrifuged and three phases were observed–2.10 gr supernatant, 0.22 gr of an intermediate phase (gel like) and 0.01 gr precipitate Rhamnolipid concentration in the supernatant and in the heavy phases (combined gel-like intermediate phase+precipitate) were 0.10% wt and >95% wt %, respectively. Rhamnolipids DC was 16.2.

These results of Examples 3 and 4 demonstrate highly efficient extraction of rhamnolipids from acidulated lipophilic-impurities depleted broth. On extraction with DME, DC values were 9.3 and 16.2 compared with 0.21 on extraction from about neutral broth, using the same extractant. Rhamnolipids concentrations in the extract precipitate, demonstrating highly efficient purification and concentration.

Example 5

Foaming Properties

An about neutral broth was extracted, as in Example 1, to form a first extract (Step 1) and a raffinate. The raffinate was acidulated to pH 3.5 and extracted, as in Example 3, to form a second extract (Step 2) and a second raffinate. This second raffinate was extracted to form a third extract (Step 3) and a third raffinate. This third raffinate was extracted to form a fourth extract (Step 4) and a fourth raffinate. Each of the extracts was added to water at a 1:8 dilution and the pH was adjusted to about 7. The formed solutions had no color or only a light yellow one.

Each diluted sample was shaken for ~10 seconds and the foaming generated by the shaking was observed for a couple of hours. It was compared to that of a commercial dish soap/water solution with the same dilution. The results are summarized in the following table.

| Seconds after shaking | Relative foam volumes | | | | |
|---|---|---|---|---|---|
| | Step 1 extract | Step 2 extract | Step 3 extract | Step 4 extract | Soap |
| 0 | 1.5 | 6 | 3.5 | 1.5 | 6 |
| 30 | 1 | 5.5 | 3 | 1 | 5.5 |
| 60 | 1 | 5.5 | 3 | 1 | 5.5 |
| 90 | 1 | 5 | 3 | 1 | 5 |
| 600 | 1 | 5 | 2.5 | 0.5 | 5 |

| Seconds after shaking | Relative foam volumes | | | | |
|---|---|---|---|---|---|
| | Step 1 extract | Step 2 extract | Step 3 extract | Step 4 extract | Soap |
| 5400 | 0.5 | 3 | 1.5 | 0 | 5 |
| 10800 | 0.5 | 1 | 0.5 | 0 | 5 |

The extract of Step 1 has only little rhamnolipids, since it is a result of extracting at about neutral pH, where rhamnolipids DC is small. Excellent foaming is shown by the extract of the second step—the first one extracted at acidic pH. The foam volume was similar to that of the dish soap, but the soap of the former appeared to have a higher density. The volume of Step 3 foam was somewhat smaller and that of Step 4 was similar to that of Step 1. This decrease in foam volume probably indicates a lower concentration of rhamnolipids, since the majority was extracted in Step 2.

These results demonstrate the high foaming efficiency of rhamnolipids purified according to the method of the invention.

Thus, the scope of the invention shall include all modifications and variations that may fall within the scope of the attached claims. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for production of a rhamnolipid, comprising
   (i) providing an aqueous fermentation medium comprising a carbon source and a nitrogen source;
   (ii) culturing in said fermentation medium an organism capable of producing a rhamnolipid, wherein said carbon source is metabolized to form a fermentation broth having a pH greater than 5 and comprising at least one rhamnolipid, at least one lipophilic impurity, and at least one hydrophilic impurity;
   (iii) extracting at least one lipophilic impurity from said fermentation broth with a first extractant to form (a) a lipophilic-impurity-depleted fermentation broth comprising the at least one rhamnolipid and (b) a first extract comprising said first extractant and said at least one lipophilic impurity;
   (iv) separating the first extractant and the at least one lipophilic impurity from the first extract;
   (v) acidulating said lipophilic-impurity-depleted fermentation broth to form an acidulated lipophilic-impurity-depleted aqueous medium of pH less than 5 comprising the at least one rhamnolipid;
   (vi) extracting the at least one rhamnolipid from said acidulated lipophilic-impurity-depleted aqueous medium with a second extractant to obtain a second extract comprising said second extractant and the at least one rhamnolipid; and
   (vii) separating the at least one rhamnolipid from said second extract to obtain a purified rhamnolipid;
   wherein said first extractant, said second extractant, or both comprise at least one of (a) a hydrocarbon having a boiling point under 20° C. at atmospheric pressure, and (b) an oxygenated organic compound having a boiling point under 20° C. at atmospheric pressure, wherein said oxygenated organic compound has a Hansen solubility parameter polarity component in the range between 2 Mpa$^{0.5}$ and 8 Mpa$^{0.5}$ and a Hansen solubility parameter H-bond component in the range between 2 Mpa$^{0.5}$ and 8 Mpa$^{0.5}$.

2. A method according to claim 1, wherein said at least one rhamnolipid comprises one rhamnose moiety in combination with two fatty acid chains and/or two rhamnose moieties in combination with two fatty acid chains.

3. A method according to claim 1, wherein rhamnolipid concentration in said fermentation broth having a pH greater than 5 is in the range between 1 g/l and 70 g/l.

4. A method according to claim 1, wherein said first extractant, said second extractant or both comprise said oxygenated organic compound and an olefin with a boiling point under 20° C. while at atmospheric pressure.

5. A method according to claim 1, wherein said first extractant comprises an olefin and said second extractant comprises said oxygenated organic compound.

6. A method according to claim 1, wherein said separating said first extractant, said separating said second extractant, or both comprises evaporation.

7. A method according to claim 6, further comprising liquefying at least a fraction of the separated first and/or separated second extractant, wherein said liquefying comprises subjecting said at least a fraction of the separated first and/or separated second extractant to a refrigerant circuit.

8. A method according to claim 7, wherein a refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

9. A method for production of a rhamnolipid, comprising
   (i) providing an aqueous fermentation medium comprising a carbon source and a nitrogen source;
   (ii) culturing in said fermentation medium an organism capable of producing a rhamnolipid, wherein said carbon source is metabolized to form a fermentation broth having a pH greater than 5 and comprising at least one rhamnolipid, at least one lipophilic impurity and at least one hydrophilic impurity;
   (iii) acidulating said fermentation broth to form an acidulated aqueous medium of pH less than 5;
   (iv) extracting the at least one rhamnolipid and the at least one lipophilic impurity from said acidulated aqueous medium with a first extractant, thereby obtaining a hydrophilic-impurity-depleted first extract comprising the at least one rhamnolipid, the at least one lipophilic impurity and the first extractant;
   (v) separating said first extractant from said at least one rhamnolipid and said at least one lipophilic impurity in said first extract to obtain a separated medium comprising said at least one rhamnolipid and said at least one lipophilic impurity;
   (vi) adjusting the pH of the separated medium to a pH greater than 5; and
   (vii) extracting the at least one lipophilic impurity from said pH-adjusted separated medium with a second extractant to obtain purified rhamnolipid wherein said first extractant, said second extractant, or both comprise at least one of (a) a hydrocarbon having a boiling point under 20° C. while at atmospheric pressure and (b) an oxygenated organic compound having a boiling point under 20° C. at atmospheric pressure, wherein said oxygenated organic compound has a Hansen solubility parameter polarity component in the range between 2

$MPa^{0.5}$ and 8 $MPa^{0.5}$ and a Hansen solubility parameter H-bond component in the range between 2 $MPa^{0.5}$ and 8 $MPa^{0.5}$.

10. A method according to claim 9, wherein said extracting the at least one lipophilic impurity comprises forming a second extract comprising the second extractant and the at least one lipophilic impurity.

11. A method according to claim 10, further comprising separating the second extractant and the at least one lipophilic impurity from the second extract.

12. A method according to claim 9, wherein said at least one rhamnolipid comprises one rhamnose moieties in combination with two fatty acid chains, and/or two rhamnose moieties in combination with two fatty acid chains.

13. A method according to claim 9, wherein rhamnolipid concentration in said fermentation broth is in the range between 1 g/l and 70 g/l.

14. A method according to claim 9, wherein said separating said first extractant comprises evaporation.

15. A method according to claim 14, further comprising liquefying at least a fraction of the separated first extractant, wherein said liquefying comprises subjecting said at least a fraction of the separated first extractant to a refrigerant circuit.

16. A method according to claim 15, wherein a refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R-406a, R-410a, R-414a, R-500, R-502, R-503, R-1301, and ammonia.

17. A method for the production of a rhamnolipid, comprising
(i) providing a fermentation medium comprising a carbon source and a nitrogen source;
(ii) culturing in said fermentation medium an organism capable of producing a rhamnolipid, wherein said carbon source is metabolized to form a fermentation broth having a pH greater than 5 and comprising at least one rhamnolipid, at least one lipophilic impurity, and at least one hydrophilic impurity;
(iii) extracting at least one lipophilic impurity from said fermentation broth with a first extractant, whereby (a) a lipophilic-impurity-depleted fermentation broth comprising the at least one rhamnolipid and (b) a first extract comprising said first extractant and said at least one lipophilic impurity are formed;
(iv) separating said first extractant and said at least one lipophilic impurity from said first extract;
(v) acidulating said lipophilic-impurity-depleted fermentation broth to a pH less than 5, whereby a rhamnolipid-enriched phase is formed; and
(vi) separating said rhamnolipid-enriched phase from the acidulated fermentation broth wherein said first extractant, said second extractant, or both comprise at least one of (a) a hydrocarbon having a boiling point under 20° C. while at atmospheric pressure and (b) an oxygenated organic compound having a boiling point under 20° C. at atmospheric pressure, wherein said oxygenated organic compound has a Hansen solubility parameter polarity component in the range between 2 $MPa^{0.5}$ and 8 $MPa^{0.5}$ and a Hansen solubility parameter H-bond component in the range between 2 $MPa^{0.5}$ and 8 $MPa^{0.5}$.

* * * * *